US009944699B2

(12) United States Patent
Crest et al.

(10) Patent No.: US 9,944,699 B2
(45) Date of Patent: Apr. 17, 2018

(54) IN VITRO METHOD FOR IDENTIFYING COMPOUNDS OF THE NAV 1.9 SODIUM CHANNEL INTENDED FOR THE TREATMENT OF AN INFLAMMATORY SKIN DISEASE (71) Applicants: GALDERMA RESEARCH & DEVELOPMENT, Biot (FR); CENTRE NATIONAL DE LA RECHERCHE SCIENTIFIQUE, Paris (FR); UNIVERSITE D'AIX-MARSEILLE, Marseilles (FR)

(72) Inventors: Marcel Crest, Marseilles (FR); Patrick Delmas, Vitrolles (FR); Aurélie Lonigro-Rame, Ensues la Redonne (FR); Nancy Osorio, Cavalaire sur Mer (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/757,529

(22) PCT Filed: Jun. 27, 2014

(86) PCT No.: PCT/FR2014/051642
§ 371 (c)(1),
(2) Date: May 6, 2016

(87) PCT Pub. No.: WO2014/207401
PCT Pub. Date: Dec. 31, 2014

(65) Prior Publication Data
US 2016/0340426 A1 Nov. 24, 2016

(30) Foreign Application Priority Data
Jun. 28, 2013 (FR) .................................. 13 56349

(51) Int. Cl.
C07K 16/28 (2006.01)
C12N 15/113 (2010.01)
G01N 33/50 (2006.01)
A61K 39/00 (2006.01)

(52) U.S. Cl.
CPC ............ *C07K 16/28* (2013.01); *C12N 15/113* (2013.01); *G01N 33/5023* (2013.01); *A61K 2039/505* (2013.01); *C07K 2317/24* (2013.01); *C07K 2317/54* (2013.01); *C07K 2317/55* (2013.01); *C07K 2317/569* (2013.01); *C07K 2317/622* (2013.01); *C07K 2317/76* (2013.01); *C12N 2310/11* (2013.01); *C12N 2310/14* (2013.01); *C12N 2310/141* (2013.01)

(58) Field of Classification Search
CPC .. G01N 33/566; G01N 33/6842; G01N 33/74; G01N 2333/726; G01N 2570/00; C07K 14/705; C07K 14/70571
See application file for complete search history.

(56) References Cited

U.S. PATENT DOCUMENTS

2007/0212685 A1* 9/2007 MacDonald ......... C12Q 1/6897
435/6.16

FOREIGN PATENT DOCUMENTS

WO 2007/023298 A2 3/2007

OTHER PUBLICATIONS

Origene society. Catalogue reference No. TR309619.*
Origene society. Catalogue reference No. SR307742.*
Novus Biologicals society. Catalogue reference No. H00011280-R01.*
Vanoye CD, et al.J. Gen. Physiol. 141(2):193-202. Feb. 2013. Available online at—doi/10.1085/jgp.201210919.*
Amaya F, et al. The Journal of Neuroscience. 26(50):12852-12860. Dec. 13, 2006. Available online at—DOI:10.1523/JNEUROSCI.4015-06.2006.*
Gilchrist J. and Bosmans F. Toxins. 4:620-632. 2012. Available online at—doi:10.3390/toxins4080620.*
Dib-Hajj S, et al. Trends in Neurosciences. 25(5):253-259. May 1, 2002. Available online at—https://doi.org/10.1016/S0166-2236(02)02150-1.*
Blum R, et al. Nature. 419(6908):687-693. Oct. 17, 2002. Available online at—DOI: 10.1038/nature01085.*
English Translation of the International Search Report dated Nov. 7, 2014 corresponding to International Patent Application No. PCT/FR2014/051642, 3 pages.
Strickland, I.T., et al., "Changes in the expression of Nav1.7, Nav1.8 and Nav1.9 in a distinct population of dorsal root ganglia innervating the rat knee joint in a model of chronic inflammatory joint pain," European Journal of Pain, vol. 12, No. 5, Jul. 2008, pp. 564-572.
Padilla, F., et al., "Expression and localization of the Nav1.9 sodium channel in enteric neurons and in trigeminal sensory endings: Implication for intestinal reflex function and orofacial pain," Molecular and Cellular Neurosciences, vol. 35, No. 1, Apr. 2007, pp. 138-152.
Lolignier, S., et al., "Nav1.9 Channel Contributes to Mechanical and Heat Pain Hypersensitivity Induced by Subacute and Chronic Inflammation," PLOS One, vol. 6, No. 8, Aug. 2011, pp. 1-11.
Yu, Yao-Qing, et. al., "Antisense-Mediated Knockdown of Nav1.8, but Not Nav1.9, Generates inhibitory Effects on Complete Freund's Adjuvant-Induced Inflammatory Pain in Rat," PLOS One, vol. 6, No. 5, May 2011, pp. 1-9.
Yu, F.H., et al., "Overview of the voltage-gated sodium channel family," Genome Biology, Biomed Central Ltd., vol. 4, No. 3, Article 207, Jan. 20013, 8 pages.
International Search Report and Written Opinion dated Nov. 7, 2014 corresponding to International Patent Application No. PCT/FR2014/051642, 11 pages.

(Continued)

Primary Examiner — Robert S Landsman
(74) Attorney, Agent, or Firm — Dentons US LLP (57) ABSTRACT The use of a modulator of the Nav 1.9 sodium channel is described for treating an inflammatory skin disease. Also described, is a pharmaceutical composition including a modulator of the Nav 1.9 sodium channel, and in vitro diagnostic methods based on the detection or quantification of Nav 1.9.

20 Claims, 5 Drawing Sheets (56) References Cited

OTHER PUBLICATIONS

Castle, N., et al., "Sodium Channel Inhibitor Drug Discovery Using Automated High Throughput Electrophysiology Platforms," Combinatorial Chemistry & High Throughput Screening, 2009, 12, pp. 107-122.

Zheng, W., et al., "High Throughput Assay Technologies for Ion Channel Drug Discovery," Assay and Drug Development Technologies, 2004, 2 (5), pp. 543-555.

Bosmans, F., et al., "Functional properties and toxin pharmacology of a dorsal root ganglion sodium channel viewed through its voltage sensors," J Gen Physiol, 2011, 138 (1), pp. 59-72.

Caterall, W.A., et al., "International Union of Pharmacology. XLVII. Nomenclature and Structure-Function Relationships of Voltage-Gated Sodium Channels," Pharmacological Reviews, 2005, 57 (4), pp. 397-409.

Wilkin, J., et al., "Standard classification of rosacea: Report of the National Rosacea Society Expert Committee on the Classification and Staging of Rosacea," J. Am. Acad. Dermatol., 2002, 46 (4), pp. 584-587.

\* cited by examiner

IN VITRO METHOD FOR IDENTIFYING COMPOUNDS OF THE NAV 1.9 SODIUM CHANNEL INTENDED FOR THE TREATMENT OF AN INFLAMMATORY SKIN DISEASE

CROSS-REFERENCE TO PRIOR APPLICATIONS

This application is a National Stage of PCT/FR2014/051642, filed June 27, 2014, and designating the United States (published on Dec. 31, 2014, as WO 2014/207401 A1), which claims priority under 35 U.S.C. § 119 to French Patent Application No. 1356349, filed Jun. 28, 2013, each hereby expressly incorporated by reference in its entirety and each assigned to the assignee hereof.

FIELD OF THE INVENTION

The invention relates to the treatment and to the diagnostic of inflammatory skin diseases, in particular rosacea.

BACKGROUND OF THE INVENTION

Inflammatory skin diseases encompass many pathologies such as rosacea, psoriasis, contact eczema, atopic dermatitis, or further pruritus.

Rosacea is a chronic and gradual common inflammatory dermatosis related to vascular disorders. It mainly affects the central portion of the face and is characterized by reddening of the face accompanied by hot flushes, facial erythema, papules, pustules, telangiectasia and sometimes ocular lesions called ocular rosacea. In extreme cases, in particular in humans, hypertrophy is observed at the nasal level called rhinophyma. Rosacea occurs between 25 and 70 years old and develops over several years with remission phases and exacerbation phases. Rosacea is much more common in persons with a pale complexion and particularly affects women. However, the most severe attacks are generally observed in men. Rosacea is classified in 4 sub-types depending on various clinical characteristics (Wilkin J et al., JAAD, 2002, 46: 584-587): erythematotelangiectatic rosacea (sub-type 1), papulo-pustular rosacea (sub-type 2), phymatous rosacea (sub-type 3) and ocular rosacea (sub-type 4). More rare forms of rosacea also exist such as the granulomatous variant which is characterized by papules or yellow, brown or red indurated nodules, and by monomorphic lesions at the papules.

The pathological signs of rosacea vary according to the sub-type of the disease. Nevertheless, it is noted that local inflammatory reactions and vascular hyperactivity are constant signs of rosacea.

The pathogenesis of rosacea is poorly known and may involve several factors. The disease may be caused or promoted by the presence of follicular microorganisms such as bacteria and mites *Demodex Folliculorum*, an aberrant innate immune response, an abnormal vascular reactivity and hypersensitivity to environmental stimuli such as exposure to UVs, sudden changes in temperature, consumption of hot drinks, spiced dishes and alcohol, strong emotions (stress, embarrassment, anger . . . ).

Conventionally, rosacea is treated orally or via a topical route with antibiotics such as tetracyclines, erythromycin, clindamycin, but also by vitamin A, salicylic acid, azelaic acid, sulfur sulfacetamide, metronidazole or by isotretinoin in severe forms. The available therapies may have unpleasant secondary effects for the patient such as irritations and their effectiveness may be limited towards certain symptoms or rosacea sub-type. Finally, these treatments generally aim the symptoms of the disease without treating the cause thereof.

Psoriasis is a chronic dermatosis, which evolves with eruptions or with fits, which affects about 2% of the population. Psoriasis is characterized by epidermal hyperproliferation (accelerated renewal of the epidermis) associated with keratinization disorders. Psoriasic lesions generally appear as erythemato-squamous plaques, often pruriginous plaques. Infiltration of leukocytes and moderate inflammation of the dermis and of the epidermis is generally observed at the lesions, which suggests that psoriasis would be a self-immune disease. Psoriasis frequently affects friction areas such as knees, elbows and the lumbar region as well as the scalp, the hands and the feet. Several forms of psoriasis are distinguished (guttate psoriasis, pustular psoriasis, . . . ), plaque psoriasis (or vulgar psoriasis) being the most common form. Etiology of psoriasis at the present time remains poorly known. One case out of two seems to be of family origin. Various predisposition genes have been discovered. Recent studies suggest that psoriasis also results from immune anomalies. Finally, psoriasis may be triggered or worsened by a certain number of factors such as psychological stress, overworking, alcohol, food diet, overweight, certain infections or the taking of drugs. Local treatments and phototherapy are used for moderate forms of psoriasis. Systemic treatments are reserved for severe forms of psoriasis. These treatments have variable effectiveness and may induce bothersome secondary effects.

Eczema groups pruriginous erythemato-vesicular inflammatory dermatoses. These pathologies generally develop in several phases: An erythematous phase, a vesicular phase, an exudation phase and a desquamation phase. Nummular eczema, contact eczema which is induced by an allergic reaction towards an exogenous agent, and atopic dermatitis are distinguished inter alia.

Atopic dermatitis (also called atopic dermatitis or atopic eczema) is a chronic dermatosis, evolving with eruptions and which essentially affects children, in particular newly born children. Atopic dermatitis is characterized by significant skin dryness (xerosis), by papular or vesicular, squamous erythematous inflammatory lesions with possibly cracks and lichenification of lesions. Atopic dermatitis affects the convexities of the cheeks, of the limbs and of the scalp in newly born children. In older children and in adults, the lesions are essentially located at the folds. Just like rosacea and psoriasis, pathogenesis of atopic dermatitis is poorly known. Genetic predisposition and/or an immune anomaly is often put forward. Certain factors may cause or worsen eruptions of atopic dermatitis: Food diet (egg, dairy product, peanut), stress, exposure to certain environmental pollutants or irritants (mites, pollens, water, limestone, perfumes, metals . . . ).

The treatment of atopic dermatitis is essentially symptomatic. It may comprise the local application of corticoids and of emollient. Anti-histaminics may be prescribed for relieving pruritus.

Finally, pruritus is a functional disorder which may be defined as a "sensation which causes the need to scratch oneself". It may be localized or generalized. This is a frequent symptom, in particular of inflammatory dermatoses with skin lesions such as psoriasis and atopic dermatitis. Nevertheless, certain prurituses are not associated with specific skin lesions (pruritus "sine materia"). Pruritus may then be caused by a general affection, be of neurological or psychological origin or be associated with skin dryness (xerosis). The pruritus may be caused or worsened by hypersensitivity to external factors (chemicals, temperature and humidity variations, hard water . . . ). In certain cases, the pruritus is a neurological sign sustained and/or amplified by a local inflammatory reaction resulting from the scratching. There does not exit any general treatment of pruritus.

At the present time, therefore there still exists a need for new treatments against inflammatory skin diseases, in particular rosacea.

The voltage-dependent sodium channels are the essential actors for initiating and propagating action potentials at the so-called "excitable" cells. These sodium channels are mainly expressed at the neurones of the central and peripheral nervous system and at muscle cells. These are transmembrane proteins comprising a large alpha ($\alpha$) sub-unit of about 260 kDa associated with one or several beta sub-units from 33 to 38 kDa. The alpha sub-unit forms the core of the channel and comprises four homologous membrane domains (I-IV), each consisting of 6 transmembrane segments (S1-S6). The membrane domains of the alpha sub-unit are connected together by large intracellular loops which comprise many regulation sites. The alpha sub-unit is responsible for the conductance and selectivity properties of the channel while the beta sub-units are involved in the stabilization and in the kinetic properties of the channel. To this day, 10 isoforms for the alpha sub-unit have been identified in humans. The name assigned to these isoforms contains the symbol of the transported ion (Na), with as an index the regulator element (the voltage v). The figures which follow designate the sub-family of genes and the number associated with the relevant isoform. To this day, the main sub-family of genes comprises the Nav 1.1 to Nav 1.9 isoforms. An additional isoform, further away. Nax has also been identified. The sequence identity percentage between the different isoforms Nav 1.1 to Nav 1.9 is of at least 45%. The isoforms Nav 1.1 to Nav 1.9 are inter alia differentiated by their sensitivity to tetrodotoxin (TTX), a very powerful and selective blocker of sodium channels, and by their tissue distribution. The isoforms Nav 1.1 to Nav 1.4, Nav 1.6 and Nav 1.7 are said to be sensitive to TTX with EC50s of the order of one nanomolar. The isoforms Nav 1.5, Nav 1.8 and Nav 1.9 are considered, as for them, as resistant to TTX. In this respect, the EC50 of the TTX for Nav 1.9 is of about 200 µM. As regards tissue distribution, the isoforms Nav 1.1, Nav 1.2, Nav 1.3 and Nav 1.6 are mainly expressed at the central nervous system. The isoform Nav 1.4 is mainly expressed at skeletal myocytes while Nav 1.5 is essentially present, in adult individuals, at the cardiac myocytes. Finally, the isoforms Nav 1.7, Nav 1.8 and Nav 1.9 are expressed at the peripheral nervous system (PNS). Nav 1.9 was mainly detected at the sensitive neurones of spinal ganglia where it would play a role in the perception of pain (nociception). Finally, Nax is expressed at the heart, the uterus, the smooth muscle, astrocytes and certain neurones of the hypothalamus and of the central nervous system. For a review relating to the voltage-dependent sodium channels, reference may be made to Yu and Caterall, Genome Biology, 2003, 4: 207 or Caterall et al., Pharmacological Reviews, 2005, 57:397-409.

To the knowledge of the Applicant, no link has been established in the state of the art between the expression of a Nav isoform, in particular Nav 1.9, and inflammatory skin diseases.

SUMMARY OF THE INVENTION

The object of the invention is the use of a modulator of the Nav 1.9 sodium channel in the treatment or prevention of an inflammatory skin disease. The inflammatory skin disease may be selected from rosacea, psoriasis, pruritus, contact eczema and atopic dermatitis. Preferably, the inflammatory skin disease is selected in the group consisting of erythematotelangiectatic rosacea (subtype I), papulopustular rosacea (subtype II), phymatous rosacea (subtype III), ocular rosacea (subtype IV) and a granulomatous variant of rosacea.

In certain embodiments, the Nav 1.9 sodium channel modulator is selected from a modulator of the activity of the sodium channel Nav 1.9, for example an inhibitor of Nav 1.9, and a modulator of the expression of the Nav 1.9 sodium channel.

In certain embodiments, the Nav 1.9 modulator is selected from an inorganic molecule, a toxin, a protein, a peptide, an organic synthetic molecule, preferably having a molecular weight of at most 1,000 g.mol$^{-1}$, an antibody directed against Nav 1.9, preferably a chimeric or humanized, human, monoclonal antibody and a molecule comprising a fragment of an antibody directed against Nav 1.9 such as ScFv, VH, V$_H$H, V$_{NAR}$, a Fab', a F(ab')2, a bispecific antibody such as a diabody, and the humanized or chimeric versions thereof.

In certain embodiments, the modulator of the expression of Nav 1.9 is an inhibitor of the translation or transcription of the Nav 1.9 gene, or a compound capable of inducing catabolism of Nav 1.9. As an example, the modulator of Nav 1.9 may be selected from a micro-RNA (miRNA), an interfering RNA such as a small interfering RNA (SiRNA) or a small hair pin RNA (shRNA), an antisense RNA and an oligonucleotide blocking a splicing site.

An additional object according to the invention is a pharmaceutical composition for a use in the treatment or prevention of an inflammatory skin disease, said composition comprising a modulator of the Nav 1.9 sodium channel and a pharmaceutically acceptable excipient. The inflammatory skin disease and the modulator of Nav 1.9 are as described earlier. The pharmaceutical composition may be administered orally or via a topical route, for example via a cutaneous or ocular route.

The invention also relates to a screening method in vitro for evaluating, screening or selecting a drug candidate for treating or preventing an inflammatory skin disease, preferably a rosacea, said method comprising:
  incubating a cell capable of expressing Nav 1.9 with a compound.
  determining the effect of the compound on the expression or the activity of Nav 1.9, and
  selecting the compound as a candidate drug for treating or preventing the inflammatory skin disease if the drug is capable of inhibiting or reducing the expression or the activity of Nav 1.9.

The inflammatory skin disease may be selected from a rosacea, psoriasis, pruritus, contact eczema and atopic dermatitis. Preferably, the inflammatory skin disease is a rosacea.

An additional object according to the invention is a method in vitro for diagnosing an inflammatory skin disease, preferably a rosacea, in a patient which may be affected therewith comprising the detection or the quantification of the expression or of the activity of Nav 1.9 in a biological sample from the patient affected therewith. In certain embodiments, the method according to the invention comprises the steps of:
  (a) detecting or quantifying the expression or the activity of Nav 1.9 in a biological sample of the patient, preferably a skin sample, and (b) comparing the expression or the activity of Nav 1.9 obtained in step (a) with the expression or the activity of Nav 1.9 either detected or quantified in one or several biological samples, preferably skin samples, from one or several control subjects, preferably healthy subjects.

The inflammatory skin disease may be selected from a rosacea, psoriasis, pruritus, contact eczema and atopic dermatitis. Preferably, the inflammatory skin disease is a rosacea.

Another object according to the invention is a method in vitro for evaluating the effectiveness of a therapeutic treatment of an inflammatory skin disease, preferably a rosacea, in a patient comprising the steps of:
(a) detecting or quantifying the expression or the activity of Nav 1.9 in a biological sample of the patient, preferably a skin sample, before treatment, and
(b) detecting or quantifying the activity or the expression of Nav 1.9 in a biological sample of the patient, preferably a skin sample, after treatment, and
(c) comparing the expression or the activity of Nav 1.9 of step (a) with that of step (b).

The inflammatory skin disease may be selected from a rosacea, psoriasis, pruritus, contact eczema and atopic dermatitis. Preferably, the inflammatory skin disease is a rosacea.

The object of the invention is also a method in vitro for tracking the progression of an inflammatory skin disease, in a patient, comprising the steps of
(a) detecting or quantifying the activity or the expression of Nav 1.9 in a first biological sample of the patient, preferably a skin sample, at a time t1,
(b) detecting or quantifying the expression or the activity of Nav 1.9 in a second biological sample, preferably a skin sample, at a time t2 after the time t1, and
(c) comparing the expression or the activity of Nav 1.9 of step (b) with that of step (a).

The inflammatory skin disease may be selected from a rosacea, psoriasis, pruritus, contact eczema and atopic dermatitis. Preferably, the inflammatory skin disease is a rosacea.

In particular embodiments, the methods according to the invention described above are characterized by one or several of the following characteristics:
(i) the biological samples are selected from dermis samples, epidermis samples and dermis and epidermis samples, preferably histological sections, and/or
(ii) the method comprises the detection or the quantification of the expression of Nav 1.9 in biological samples, and/or
(iii) the expression of Nav 1.9 is detected or quantified by means of an antibody directed against Nav 1.9 in biological samples, preferably by immunohistochemistry.

FIGURES

FIG. 3 shows the localized expression of Nav 1.9 at an isolated nerve fiber of the healthy dermis, in proximity of the epidermis-dermis interface. FIG. 3A shows the marking with the anti-peripherin antibody. FIG. 3B shows the marking with the antibody 3881. The co-marking of peripherin and of Nav 1.9 is illustrated in FIG. 3C. Basal Mb: basal membrane, kera: keratinocyte of the epidermis, Ext: external.

FIG. 4 shows the localized expression of Nav 1.9 at sensitive fibers innervating the hair follicle (healthy skin). FIG. 4A shows the marking with the anti-peripherin antibody. FIG. 4B shows the marking with the antibody 3881.1. The co-marking of peripherin and of Nav 1.9 is illustrated in FIG. 4C.

FIGS. 5, 6 and 7 show the immuno-marking of skin samples from patients suffering from rosacea. FIG. 5 corresponds to a dermis section and FIG. 6 shows a hair follicle. FIG. 7 shows the immuno-marking of a skin section of the "dermis-epidermis". FIGS. 5A, 6A and 7A: marking with the anti-peripherin antibody. FIGS. 5B, 6B and 7B: marking with the antibody 3881.1. The co-marking is shown in FIGS. 5C, 6C and 7C. Nav 1.9 is detected with the antibody 3881.1 at the sensitive nerve fibers in the dermis, at the hair follicle and at the interface of the dermis and of the epidermis in the skin of patients affected with rosacea.

FIGS. 8A and 8B show the results of experiments for releasing CGRP (calcitonin gene-related peptide) in primary neurone cultures, from spinal ganglia of wild mice (WT) or invalidated for the Nav 1.9 gene (KO), after treatment (S) with capsaicin (15 min, 300 nM) or without any treatment with capsaicin (NS) (see Example 3 hereafter). FIG. 8A shows the concentrations of CGRP (pg/ml) detected in the supernatant for each tested cell culture as well as the average CGRP concentrations for each group of experiments (black bar). FIG. 8B shows the ratios (in %) of the average CGRP concentration in the supernatant, after stimulation, over the average concentration, before stimulation, for cell cultures from WT and KO mice. An increase of about 43.5% of the CGRP concentration is observed after treatment with capsaicin, for cell cultures obtained from WT mice. On the other hand, no increase is observed for neurone cultures from KO mice after stimulation with capsaicin.

DETAILED DESCRIPTION OF THE INVENTION

The Applicant has shown by immuno-marking experiments that the Nav 1.9 sodium channel is expressed by the sensitive fibers of the skin (Example 1). Strong expression of the Nav 1.9 sodium channel was detected at the sensitive nerve fibers of skin samples from patients affected with rosacea (Example 2). The Applicant has moreover shown that Nav 1.9 controls the releasing of the CGPR peptide (calcitonin gene-related peptide), a mediator of the inflammation by the sensitive neurones following stimulation with capsaicin. These results very strongly suggest involvement of Nav 1.9 in the potentialization of the inflammatory response consecutive to stimulation of the sensitive fibers, in particular at the skin. The Applicant has therefore shown, for the first time that Nav 1.9 is a therapeutic target of choice for the treatment of inflammatory skin diseases, in particular rosacea.

Therapeutic Use of a Modulator of the Nav 1.9 Sodium Channel, Pharmaceutical Compositions and Treatment Methods The object of the present invention is therefore the use of a modulator of the Nav 1.9 sodium channel for treating or preventing an inflammatory skin pathology.

In the sense of the invention, an "inflammatory skin pathology" or an "inflammatory skin disease" designates a disease or a disorder affecting the skin characterized in that it is associated with, caused by, or may involve an inflammatory reaction. The inflammatory skin pathology may affect any portion of the skin, including the face, the scalp and the ocular region, in particular the eyelids.

In certain embodiments, the inflammatory reaction is a local neurogenic inflammation i.e. triggered, at least partly, by a neurological response, in particular by the local release of pro-inflammatory neuropeptides such as the substance P and the CGRP peptide.

In other embodiments, the inflammatory skin disease is initiated by a neurological disorder as this may be observed in certain cases of pruritus.

The inflammatory skin pathologies according to the invention encompass, without being limited thereto, a rosacea, psoriasis, pruritus, and an eczema such as contact eczema and atopic dermatitis.

In the sense of the invention, eczema comprises atopic eczema (also called atopic dermatitis or atopic dermatitis), contact eczema and nummular eczema. A preferred form of eczema is atopic dermatitis.

The rosacea comprises, without being limited thereto, erythematotelangiectatic rosacea (subtype 1), papulopustular rosacea (subtype 2), phymatous rosacea (subtype 3) and ocular rosacea (subtype 4) and granulomatous variants of rosacea.

A preferred form of pruritus is a pruritus associated with an inflammatory dermatosis and/or with a skin lesion.

In preferred embodiments, the inflammatory skin pathology is a rosacea, in particular a rosacea of subtype 1 (erythematotelangiectatic rosacea), a rosacea of subtype 2 (papulopustular rosacea), a rosacea of subtype 3 (phymatous rosacea), a rosacea of sub-type 4 (ocular rosacea) or a granulomatous variant of rosacea.

In the sense of the invention, the term of "treatment" refers to the fact of slowing or blocking the development of a disease or the fact of treating, attenuating or slowing down one or several symptoms of the disease, or further the fact of healing said disease. Prevention of a disease as for it refers to the fact of preventing the occurrence or slowing down the occurrence of the disease or of one or several symptoms associated with the disease.

The symptoms associated with the inflammatory skin disease may for example be a skin lesion, skin dryness, redness or an erythema, sensations of burning, prickling or skin tightness, itching sensations, hypersensitivity to an external stimulus (temperature, humidity, UV) and vasodilation. In a preferred embodiment, this is a symptom associated with any of the subtypes of rosacea as described earlier.

In the sense of the present invention, by "Nav 1.9", "Nav 1.9 sodium channel" or "Nav 1.9 sodium channel", is meant the sub-unit Nav 1.9 as such or a voltage-dependent sodium channel ($Na^+$) comprising the Nav 1.9 alpha sub-unit. Preferably, this is the human Nav 1.9 sub-unit. Nav 1.9 is coded by the gene SCN11A, also called NaN, SCN12A and SNS-2 in the literature. The identification number of the human Nav 1.9 gene in the base of genes of NCBI is 11289 (NCBI Gene ID). The protein sequence of human Nav 1.9 is notably described in the base of sequences UniProt (sequence reference: Q9U133) and that of the NCBI (NCBI sequence reference: NP_054858). As regards the mRNA for Nav 1.9, see the NCBI reference sequence: NM_014139.

An "Nav 1.9 sodium channel modulator" refers to any compound capable of modulating the activity or the expression of Nav 1.9.

A modulator of the expression of the Nav 1.9 sodium channel refers to any compound capable of modifying, preferably reducing the expression level of Nav 1.9 in a cell expressing Nav 1.9. Preferably, the modulator of the expression of Nav 1.9 is a compound capable of reducing the membrane expression of Nav 1.9 in a cell (i.e. reducing the expression of Nav 1.9 at the cell membrane of the cell). It is considered that a compound is a modulator of the expression of Nav 1.9 when the incubation of this compound with a cell expressing endogenously or in a recombinant way Nav 1.9 causes a variation of at least 10%, preferably of at least 20% of the expression level of Nav 1.9 in the cell as compared with a cell which has not been incubated with said compound. A modulation of at least 20% encompasses a modulation of at least 40%, of at least 60%, of at least 80%, of at least 100%. Preferably the modulation corresponds to the reduction in the expression level of Nav 1.9 or a reduction of the activity of Nav 1.9.

A modulator of the expression of Nav 1.9 is generally a compound capable of inhibiting the translation or the transcription of the Nav 1.9 gene, or a compound capable of inducing the catabolism of Nav 1.9.

In certain embodiments of the invention, the modulator of the expression of the Nav 1.9 sodium channel may thus be selected from among an inhibitor of the transcription of the Nav 1.9 gene, an inhibitor of the translation of the mRNA of Nav 1.9, a blocker of the splicing of pre-messenger RNA of Nav 1.9, a compound capable of altering the ripening of Nav 1.9, or further a compound capable of inducing the catabolism and/or the internalization of Nav 1.9.

As an example, the modulator of the expression of the Nav 1.9 sodium channel may be selected from a micro-RNA (miRNA), an interferent RNA such as a small interferent RNA (siRNA) or a small hairpin RNA (shRNA), an antisense RNA, or an oligonucleotide blocking a splicing site.

The sequence of the mRNA of Nav 1.9 being known, one skilled in the art is capable of designing oligonucleotides capable of inhibiting the translation. Alternatively, one skilled in the art may use oligonucleotides commercially available, like vectors of shRNA (for example with the catalogue reference TR309619) and the siRNAs (for example of catalogue reference SR307742) marketed by Origene society. Interferent RNAs directed against Nav 1.9 are also marketed by Novus Biologicals society (catalogue reference: H00011280-R01). One skilled in the art may also be inspired by antisense RNAs aiming the murine Nav 1.9 sodium channel which are described in the literature (see for example Yu et al., PlosOne 6(5): e19865).

A "modulator of the activity of the Nav 1.9 sodium channel" refers to any compound capable of modifying, preferably reducing at least partly the activity of the Nav 1.9 sodium channel, i.e. its conductance, in other words its permeability to $Na^+$ ions, in response to an action potential (depolarization of the cell membrane). Preferably, this is an antagonist (or inhibitor) of the Nav 1.9 channel. An inhibitor of the Nav 1.9 sodium channel encompasses, inter alia, compounds capable of stabilizing the Nav 1.9 sodium channel in its "closed" conformation or in its "inactive" conformation, a compound capable of increasing the excitability threshold of the Nav 1.9 sodium channel, for example by increasing the value of the membrane depolarization to be applied for causing the opening of the Nav 1.9 channel, compounds capable of rapidly deactivating the Nav 1.9 sodium channel subsequent to an action potential, or further a compound capable of sterically blocking the passage of Na$^+$ ions through the Nav 1.9 sodium channel.

Preferably, these are specific antagonists of the Nav 1.9 channel, i.e. inhibitors capable of more effectively inactivating the Nav 1.9 sodium channel than another voltage-dependent sodium channel. As an example, the modulator according to the invention is specific to Nav 1.9 as compared with Nav 1.3, Nav 1.5, Nav 1.7, and/or Nav 1.8, preferably relatively to Nav 1.5 and/or Nav 1.7.

The specific antagonists of the Nav 1.9 channel encompass compounds which are capable of inactivating Nav 1.9 and which have larger binding affinity, for example a smaller dissociation constant (Kd) for Nav 1.9 than for another sodium channel such as Nav 1.3. Nav 1.5, Nav 1.7 and/or Nav 1.8. Typically, it is considered that an inhibitor compound is specific to the Nav 1.9 sodium channel relatively to a second sodium channel if the dissociation constant (Kd) of this inhibitor compound for Nav 1.9 is at least 10 times less, preferably at least 100 times and even more preferably at least 1,000 times less than the dissociation constant (Kd) for the second sodium channel. The dissociation constants may be determined by methods well known to one skilled in the art, for example by surface plasmon resonance. The dissociation constant of a therapeutic antibody directed against Nav 1.9 may have a Kd for Nav 1.9 of the order of $10^{-9}$ to $10^{-12}$ M.

The modulators of the activity of the Nav 1.9 sodium channel may be selected from any compound having the desired activity. This may be an inorganic molecule, for example a cation, a toxin, a protein, a peptide, an organic synthetic molecule, preferably having a molecular weight of at most 1,000 g.mol$^{-1}$, or further an antibody directed against Nav 1.9.

By antibody directed against Nav 1.9 is meant any antibody, or any protein construct comprising an antibody fragment capable of recognizing and of specifically binding to an epitope of the Nav 1.9 sodium channel, preferably human. For the therapeutic applications according to the invention, the antibody directed against Nav 1.9 is a functional antibody, i.e. an antibody capable of modulating, preferably inhibiting the activity of Nav 1.9.

An antibody directed against Nav 1.9 may be a monoclonal or polyclonal antibody. Preferably, the antibody is monoclonal. The antibody may be a chimeric, humanized or human antibody. This may be an entire immunoglobulin, i.e. having the antibody structure naturally present in blood plasma, for example, an immunoglobulin (Ig) comprising 2 light chains and 2 heavy chains or a heavy-chain antibody comprising 2 heavy chains and without any light chains such as heavy chain antibodies (HCab) from camelids or the IgNar of cartilaginous fish. As an alternative, the antibody may be a protein construct comprising a fragment, more specifically a variable portion of an immunoglobulin directed against Nav 1.9 such as an ScFv, VH, V$_H$H, V$_{NAR}$, Fab, Fab2, a bispecific antibody such as a diabody, and the humanized or chimeric versions thereof. As an example, the antibody according to the invention may be a humanized ScFv directed against Nav 1.9 fused with a human domain Fc. One skilled in the art will be able to design an antibody adapted to a therapeutic use according to the invention by routine experiments and techniques and may be inspired for this purpose by anti-Nav 1.9 antibodies described in the state of the art. He/she may for example be inspired by anti-Nav 1.9 antibodies described in the state of the art and apply humanization or chimerization methods. Alternatively, one skilled in the art may prepare functional antibodies directed against Nav 1.9 by applying the preparation method described in application WO2011/051351, the contents of which are incorporated by reference herein.

As mentioned herein before, the modulator of the activity of Nav 1.9 may be an organic molecule. Inhibitor compounds which may be able to inhibit Nav 1.9 are inter alia, described in applications WO2012125613 and WO2007047474, the contents of which are incorporated by reference.

Additional examples of Nav 1.9 sodium channel modulators are mibefradil, certain di- and tri-valent metal cations and protoxin-1.

Alternatively, one skilled in the art may apply the screening method according to the invention (see hereafter) in order to identify modulators of the Nav 1.9 sodium channel.

The object of the present invention is also a pharmaceutical composition comprising an Nav 1.9 sodium channel modulator and at least one pharmaceutically acceptable excipient. The modulator of the Nav 1.9 sodium channel may be present in the pharmaceutical composition in free form, as a salt, a solvate and/or a hydrate.

The pharmaceutical composition is intended for a use for treating an inflammatory skin disease as described earlier. The pharmaceutical composition may be administered via any suitable route, for example orally, via a parenteral route, via a subcutaneous route or topically. The pharmaceutical composition may be in any galenic form suitable for the selected administration route. For example, the pharmaceutical compositions intended for oral administration according to the invention may appear as gelatin capsules, tablets, syrup, powders or a suspension.

Preferably, the pharmaceutical composition is intended for administration via a topical route, in particular via a cutaneous route, via an intradermal route, via a hypodermal route or via an ocular route. Depending on the chemical nature of the modulator of Nav 1.9, one administration route may be preferred over another. As an example, an intradermal administration may be preferred when the modulator of Nav 1.9 is an antibody or an oligonucleotide such as a siRNA.

The pharmaceutical composition according to the invention may thus appear as an eyewash, an injectable composition, an aqueous, alcoholic or hydro-alcoholic solution, as a micellar solution, as an oil, as an pomade, as a powder, as a cream, as an ointment, as a lotion, as a milk, as a suspension, as a balm, as a shampoo, as an emulsion such as a nanoemulsion, a microemulsion, a water-in-oil (W/O) or oil-in-water (O/W) emulsion, or further a multiple emulsion, for example a triple emulsion W/O/W or O/W/O, as a gel such as a hydrogel or an organogel, as a foam or further as a composition for an aerosol. The composition may also appear as a patch, an implant or a bandage. Advantageously, the composition may appear as a pomade, a cream, a lotion or a gel.

The pharmaceutical composition according to the invention may comprise from 0.01% to 99% by weight of the modulator of the Nav 1.9 sodium channel and 1% to 99.9% by weight of at least one pharmaceutically acceptable excipient, the percentages being expressed based on the total weight of the composition. Preferably, the modulator of the Nav 1.9 sodium channel is present in an amount from 0.1% to 20% by weight, typically between 1% and 10% by weight. Thus, the pharmaceutical composition may comprise from 80% to 99.9%, typically from 90% to 99% by weight, of at least one pharmaceutically acceptable excipient. The excipient(s) present in the pharmaceutical composition is(are) selected according to the active ingredient to be formulated and to the desired galenic form. One skilled in the art may refer to the reference handbook "Handbook of Pharmaceutical Excipients", American Pharmaceutical Association, Pharmaceutical Press; 6th revised edition, 2009). One skilled in the art may moreover select the excipient(s) from excipients for cosmetic use known for being adapted to the preparation of pharmaceutical compositions intended for skin application.

The excipient(s) pharmaceutically acceptable may be selected from a filler, a thickener, a humectant like sorbitol, an oil, for example a vegetable oil, a mineral oil like Vaseline or synthetic oil like silicone oils, a wax, a surfactant, an emulsifier, a stabilizer, an electrolyte, a chelating agent such as EDTA, essential fatty acids, phospholipids, sphingolipids, a pro-penetrating agent such as propylene glycol, thermal water, floral water, an essential oil, a solvent such as an alcohol like ethanol or isopropanol, a pH regulating agent, an acid or a base, a preservative such as benzalkonium chloride, a perfume, a coloring agent and combinations thereof.

In certain embodiments, the pharmaceutical composition according to the invention may comprise an additional active ingredient. This additional active ingredient may exert a cosmetic effect and/or a therapeutic effect.

The active ingredient may for example be an emollient, a hydrating agent, a UV filter, a matifying agent, or an antioxidant. The additional active ingredient may be a pharmaceutical active ingredient. This may be a compound described in the state of the art for treating the inflammatory skin disease or a symptom of the latter. The additional active ingredient may be selected from an anti-inflammatory agent, for example a corticoid such as hydrocortisone or betamethasone or a non-steroid anti-inflammatory agent, an antibiotic, a keratolytic agent, an antiparasite, an antifungal agent, an anti-histaminic agent, an analgesic, an antiseptic agent, an anesthetic agent, an immuno-modulator, a disinfecting agent, a vitamin, for example vitamins E, A or D as well as derivatives thereof like retinoic acid.

When the pharmaceutical composition is intended for treating rosacea, the additional active ingredient may be selected from metronidazole, azelaic acid, isotretinoin, doxycycline, brimonidine and/or ivermectin.

The object of the present invention is also the use of a modulator of the Nav 1.9 sodium channel for preparing a drug intended for treating an inflammatory skin disease, preferably a rosacea.

The object of the present invention is also a modulator of the Nav 1.9 sodium channel for a use in a combination with an additional active ingredient, preferably selected from an anti-inflammatory agent, an antibiotic, a keratolytic agent, an antiparasite, an antifungal agent, an anti-histaminic agent, an analgesic, an antiseptic agent, an anesthetic agent, an immuno-modulator, a disinfecting agent, and a vitamin or a derivative thereof, for treating a skin disease, preferably rosacea. The Nav 1.9 modulator and the additional active ingredient are for simultaneous use or spread out in time.

An additional object according to the invention is a method for treating or preventing an inflammatory skin disease in a patient, comprising the administration of an effective amount of the Nav 1.9 modulator or of the pharmaceutical composition according to the invention, to the patient. Preferably, the treatment or prevention method is applied topically, for example via an ocular, cutaneous or intradermal route. In a particular embodiment, the pharmaceutical composition is preferably applied on the skin area(s) affected by the inflammatory skin disease, i.e. having at least one symptom of the disease. The dose of Nav 1.9 modulator may range from 0.0001 $g/cm^2$ to 1 $g/cm^2$ of skin, and depends on the therapeutic activity of the Nav 1.9 modulator and on the sought therapeutic effect.

In an additional embodiment, the composition is injected via an intradermal route. The unit dose to be injected may vary from 0.001 mg to 1 g of Nav 1.9 channel modulator.

The dosage and the administration frequency may vary according to characteristics of the patient, (for example his/her age, weight, gender) and on the extent and the seriousness of his/her symptoms.

As an example, when the composition is applied on the skin, the pharmaceutical composition according to the invention may be administered 1 to 2 times a day, during one to several weeks, or even several months. When the composition according to the invention is injected via an intradermal route, the administration frequency may vary from one injection every 6 months to one or several injections per week.

The object of the present invention is also a cosmetic composition comprising a modulator of the Nav 1.9 sodium channel and at least one cosmetically acceptable excipient. Preferably, this is a cosmetic composition intended to be applied on the skin, for example on the face.

Method for Screening Compounds or the Treatment of an Inflammatory Skin Disease

An additional object of the present invention is a screening method in vitro for evaluating, screening or selecting a candidate drug for the treatment or prevention of an inflammatory skin disease comprising the steps of:

incubating a cell capable of expressing Nav 1.9 with a compound, determining the effect of the compound on the expression or the activity of Nav 1.9, and selecting the compound as a candidate drug if the compound is capable of inhibiting the expression or the activity of Nav 1.9.

In the sense of the invention, "a cell" refers to an isolated cell or a set of cells such as a cell culture. The cell used may be any cell endogenously expressing or in a recombinant way Nav 1.9. As an example, the cell may be a neurone or a primary culture of neurones for example a culture of spinal neurones. This may also be a host cell such as Cos-7, CHO, BHK, and HEK-293, expressing in a stable or transient way Nav 1.9.

The inflammatory skin disease may be selected from a rosacea, psoriasis, pruritus, and an eczema such as atopic dermatitis. Preferably, the inflammatory skin disease is a rosacea. In certain embodiments, the inflammatory skin disease is selected from among erythematotelangiectatic rosacea (subtype 1), papulopustular rosacea (subtype 2), phymatous rosacea (subtype 3), ocular rosacea (subtype 4) and a granulomatous variant of rosacea.

The effect of the compound on the expression of Nav 1.9 may be determined by quantifying the Nav 1.9 protein or the messenger RNA coding for Nav 1.9. One skilled in the art may thus use well known methods for quantifying the mRNA, for example, quantitative RT-PCR, Northern blot or further techniques based on the hybridization of the target nucleic acid (messenger RNA or cDNA) with an oligonucleotide probe. Alternatively, it is also possible to use a recombinant system comprising a reporter gene, for example the gene of luciferase or of GFP, the expression of which is under the control of the promoter of the Nav 1.9 gene. The effect of the compound may then be determined by detecting the expression of the reporter gene. Alternatively, the effect of the compound may be evaluated by quantifying the Nav 1.9 protein. For this purpose, immuno-assay techniques may be used, for example an ELISA test or a radio-immunological assay (RIA), immunohistochemistry or further mass spectrometry, optionally coupled with liquid phase chromatography (LC-MS).

The effect of the compound on the activity of Nav 1.9, i.e. its possible inhibitor activity, may be determined by methods well known to one skilled in the art. This may be a test for binding to the Nav 1.9 channel, an electrophysiology test like a patch clamp, a radioactive ion inflow test (radiotracer), for example $^{22}Na^+$, or a test based on the use of fluorescent probes sensitive to voltage or on the transfer of energies between fluorescent molecules (FRET). One skilled in the art may thus be inspired by activity tests described in Castle et al., 2009, *Combinatorial Chemistry & High Throughput Screening*, 12, 107-122 and Zheng and Laszlo, 2004, *ASSAY and Drug Development Technologies*, 2(5): 543-552 for practically applying the screening method according to the invention, the contents of both of these publications being incorporated by reference herein. One skilled in the art may also be inspired from the work of Bosmans et al. (J Gen Physiol, 2011, 138(1): 59-72) which describes the obtaining of Nav 1.9-Kv1.2 chimeras and their applications in an activity test.

It is considered that the compound inhibits the expression or the activity of Nav 1.9 if the expression or activity level of Nav 1.9 in the incubated cell with the compound is at most equal to 90%, preferably at most equal to 80% of the expression or activity level of Nav 1.9 detected in a control cell which has not been incubated with the compound. An expression or an activity at most equal to 90% encompasses an expression or an activity at most equal to 80%, 70%, 60%, 50%, 40%, 30% 20%, 10%, 5% of the expression or the activity of Nav 1.9 in the control cell.

In a particular embodiment, the screening method according to the invention may comprise a step consisting of testing the selected candidate drug on an inflammatory skin disease model, preferably a model in vitro. The model is preferably a model of rosacea.

The compounds tested in the screening method according to the invention may be natural or synthetic compounds stemming from chemical libraries or banks of compounds. These may also be pre-selected compounds, for example, by screening in silico, the structure of the Nav 1.9 sodium channel being known.

Diagnostic Method In Vitro

The present invention also relates to a diagnostic method in vitro of an inflammatory skin disease in a patient which may be affected therewith, said method comprising the detection and/or the quantification of the activity and/or the expression of Nav 1.9 in a biological sample from the patient. In certain embodiments, this method comprises the steps of:
  (a) detecting or quantifying the expression or the activity of Nav 1.9 in a biological sample of the patient, preferably a skin sample.
  (b) comparing the expression or the activity of Nav 1.9 obtained in step (a) with the expression or activity of Nav 1.9 detected or quantified in one or several biological samples, preferably skin samples, from one or several control subjects.

In certain embodiments, the control subject(s) is(are) individuals suffering from the inflammatory skin disease which one wishes to diagnose in the patient. In this embodiment, it may be considered that the patient suffers from the inflammatory skin disease if the expression of the activity of Nav 1.9 determined in step (a) is at least equal to that of the control subjects. If the expression or the activity of Nav 1.9 determined in step (a) is significantly less than the one detected for control subjects, the diagnostic is negative. Finally, if the expression or the activity of Nav 1.9 determined in step (a) is only slightly less than the one determined for control subjects, the patient may be diagnosed as a risk patient, i.e. a patient who may develop the inflammatory skin disease.

In other embodiments, the control subject(s) correspond to healthy patients, i.e. to individuals who do not suffer from the inflammatory skin disease. In these embodiments, the patient is diagnosed as suffering from the inflammatory skin disease, or may suffer therefrom, if his/her biological sample has an expression or an activity for Nav 1.9 greater than that of the sample(s) from healthy patients. On the other hand, if the activity or the expression of Nav 1.9 determined in step (a) is less than or equal to that of the samples from control patients (healthy), then the diagnostic may be considered as negative. It may be considered that the sample of the patient is positive if the sample has an expression or an activity for Nav 1.9 at least 10% greater, preferably at least 20% greater than that of the sample(s) of healthy patients.

The detection or the quantification of the biological sample(s) of the control subject(s) may be concomitant with those carried out for the sample of the patient or from data collected previously and for example available in a database.

An additional object according to the invention is a method in vitro for evaluating the effectiveness of a therapeutic treatment of an inflammatory skin disease, in a patient, comprising the steps of:
  (a) detecting or quantifying the expression or the activity of Nav 1.9 in a biological sample of the patient before treatment,
  (b) detecting or quantifying the expression or the activity of Nav 1.9 in a biological sample of the patient after treatment,
  (c) comparing the expression or the activity of Nav 1.9 of step (a) with the one determined in step (b).

The effectiveness of the treatment is determined by comparing the expressions of Nav 1.9 in the samples (a) and (b). If the expression or the activity of Nav 1.9 is lower in the sample of step (b) than in the sample of step (a), this means that the treatment is effective. If there is an increase in the expression of Nav 1.9, it may be considered that the treatment is not very active or inactive depending on the magnitude of the observed variation. In certain embodiments, it is considered that the treatment has a therapeutic effect on the inflammatory skin disease if it involves a decrease in the expression or in the activity of Nav 1.9 by at least 10%, preferably by at least 20%. The biological samples, taken before treatment and after treatment, are preferably skin samples.

The object of the present invention is also a method in vitro for tracking the progression of an inflammatory skin disease in a patient comprising the steps of:
  (a) detecting or quantifying the activity or the expression of Nav 1.9 in a first biological sample, preferably a skin sample, taken from the patient at a time t1,
  (b) detecting or quantifying the activity or the expression of Nav 1.9 in a second biological sample, preferably a skin sample, taken from the patient, the second sample having been taken at a time t2 after time t1,
  (c) comparing the expression or the activity of Nav 1.9 of step (b) with the one determined in step (a).

The comparison of the expression or of the activity of Nav 1.9 in step (c) is a criterion allowing determination of the progression or of the stage of the inflammatory skin disease. It is thus possible to determine if the disease is in regression, stationary or is worsening.

If the sample of step (b) has an expression level of Nav 1.9 less than the expression or the activity determined in step (a), the conclusion may be drawn that the inflammatory skin disease is in regression. Conversely, if the sample of step (b) has an expression or an activity for Nav 1.9 greater than the one measured in the first step, the inflammatory skin disease is progressing.

In the case of chronic diseases such as rosacea, the method according to the invention also gives the possibility of anticipating the occurrence of a new fit or eruption and setting into place a prophylactic treatment.

In certain embodiments, the time t2 is posterior by at least 1 month, preferably by at least 6 months, or even by at least 1 year to time t1.

The object of the invention is also methods for generating data and/or useful information for diagnosing, and/or for predicting and/or for tracking the development of the inflammatory skin disease, in a patient, these methods may contain any of the combination of the steps described above. The object of the invention is also a method for generating data and/or useful information for determining the effectiveness of a treatment in a patient affected with an inflammatory skin disease.

In the whole of these methods according to the invention described herein before, the inflammatory skin disease may be selected from a rosacea, psoriasis, pruritus, contact eczema and atopic dermatitis.

The preferred inflammatory skin disease is a rosacea, for example erythematotelangiectatic rosacea (subtype 1), papulopustular rosacea (subtype 2) or further a granulomatous variant of rosacea.

For applying any of the methods described above, the biological sample(s) is(are) preferably skin sample(s). These may be dermis, epidermis or dermis and epidermis samples. In certain embodiments, this is a skin biopsy.

Preferably, the methods according to the invention comprise the detection or the quantification of the expression of Nav 1.9 in biological sample(s).

In the methods according to the invention, the expression of Nav 1.9 may be detected or quantified according to methods well known to one skilled in the art.

For this purpose, one skilled in the art may seek to quantify the messenger RNA coding for Nav 1.9, for example by quantitative RT-PCR and/or by hybridization techniques, for example by means of a marked probe or by the use of a DNA chip. In other embodiments, the methods according to the invention comprise the quantification of the Nav 1.9 protein in the biological samples, for example by Western blot, by mass spectrometry, by immuno-assay, in particular with ELISA, by immunohistochemistry, for example by immuno-marking with fluorescence. Preferably, the expression of Nav 1.9 is detected or quantified by detecting or quantifying the Nav 1.9 protein as such.

The activity of Nav 1.9 may also be determined or quantified according to methods well known to one skilled in the art. Application of an electrophysiology technique of the patch clamp type will be preferred, carried out on isolated cells of the biological sample or further, an indirect method based on the dosage of pro-inflammatory neuropeptides or the evaluation of the inflammatory-response (edema, redness) at the skin.

The biological sample may undergo a certain number of treatments in order to allow quantification or detection of the activity or of the expression of Nav 1.9.

As an example, in order to detect or quantify Nav 1.9 by immunohistochemistry, the biological sample may be a histological section of dermis or of dermis-epidermis which is beforehand, either cryofixed, or chemically fixed and optionally included in a resin.

As an additional example, the biological sample, preferably of the dermis, may be milled, centrifuged and then extracted in order to obtain a protein extract, from the cell membranes, adapted for applying a Western blot.

In particular embodiments, the methods according to the invention are characterized by one or several of the following features (or even all the features):
(i) the biological samples are skin samples, for example of dermis, of epidermis and of epidermis-dermis. Preferably these are histological sections, and/or
(ii) the method comprises the detection or the quantification of the expression of Nav 1.9 in biological samples, and/or
(iii) the expression of Nav 1.9 is detected or quantified by means of an antibody directed against Nav 1.9 in biological samples, preferably by immunohistochemistry.

The antibody may be a polyclonal or monoclonal antibody. Preferably, the antibody is directed against one or several epitopes included in the N-terminal end, in the intracellular loop connecting the membrane domains I and II or in the intracellular loop connecting the membrane domains II and III of human Nav 1.9. The antibody may be coupled with a detection means such as a fluorescent molecule, a chromophore or an enzyme like horseradish peroxidase (HRP), alkaline phosphatase, β-galactosidase, or glucose-6-phosphate dehydrogenase. Alternatively, the detection may be carried out by means of a secondary antibody.

The methods according to the invention may also comprise the detection of an additional marker or the evaluation of a particular symptom of the inflammatory skin disease. As an example, when the inflammatory skin disease is rosacea, the methods according to the invention may comprise the detection of an additional marker or of a symptom of rosacea such as papules, vascular hyperreactivity, erythema, or sensations of burning, prickling or itching.

Finally, the object of the invention is also the use of an antibody directed against Nav 1.9 for the diagnosis, prognosis and/or prediction in vitro of an inflammatory skin disease, or further the use of said antibody for tracking in vitro the development of an inflammatory skin disease or for evaluating in vitro the effectiveness of a drug for treating an inflammatory skin disease, the inflammatory skin disease may be selected from a rosacea, psoriasis, pruritus, contact eczema, and atopic dermatitis. The inflammatory skin disease being preferably rosacea.

Other aspects and advantages of the present invention will become apparent upon reading the examples which follow. These examples should be considered as illustrative and by no means as limiting the scope of the invention.

EXAMPLES

Example 1

Detection of the Expression of Nav 1.9 by Skin Sensitive Nerve Fibers

Detection of the expression of Nav 1.9 at skin nerve fibers was carried out by immunohistofluorescence by means of polyclonal antibodies directed against the alpha sub-unit of the human Nav 1.9 voltage-dependent sodium channel. The antibody Rbαa6 is directed against the intracellular loop binding the transmembrane domains II and III of human Nav 1.9. The antibody 3881.1 is directed against the intracellular loop I-II of Nav 1.9.

It was shown that these polyclonal antibodies are specific of human Nav 1.9. In particular, they do not bind to the Nav 1.5 and Nav 1.7 sodium channels.

Co-marking by means of an antibody directed against peripherin, a specific protein of the peripheral nerve tissue, was carried out in order to localize the nerve fibers.

Entire skin was used and the different compartments were identified and analyzed: deep dermis, dermis, dermis-epidermis interface and hair follicle.

Sampling and Preparing the Samples

The skin samples were prepared in the following way:

After disinfecting the skin, 3 mm skin biopsies were made in a healthy patient subject to local anesthesia at the biopsy site. The biopsy is then washed in PBS pH 7.2 and placed in an Eppendorf tube in liquid nitrogen. The Eppendorf is then stored at −80° C. until inclusion in the OCT matrix. The frozen 10 μm thick sections are then made.

Marking Procedure with Immunofluorescence

The sections are incubated for 1 h 30 min at room temperature in a saturation medium: PBS+3% (mass/volume) of BSA+0.3% (volume/volume) of Triton X-100. The primary antibodies (anti-Nav 1.9 or anti-peripherin) are added to the saturation medium for incubation of 12 h at 4° C. in a humid chamber. The sections are then rinsed 4 times for 15 min in PBS before 45 min of incubation at room temperature with the secondary antibodies in PBS+3% (mass/volume) of BSA in a humid chamber. Finally, the sections are rinsed 4 times for 15 min in PBS before being mounted in a mounting medium (Mowiol or Prolong Gold).

Results

Figure 1:
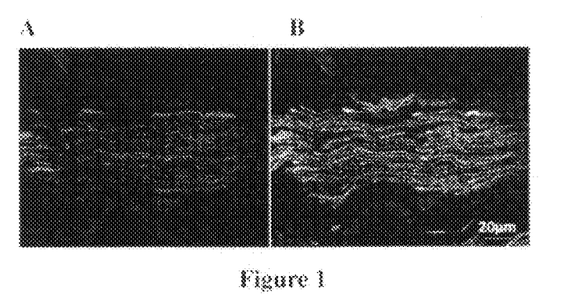
FIG. 1 show the results of immuno-marking a healthy deep dermis section with the anti-Nav 1.9 antibody Rbαa6 (FIG. 1A). Co-marking with an anti-peripherin antibody is illustrated in FIG. 1B. A significant proportion of the nerve fibers of the dermis marked with peripherin are Nav 1.9 positive.
Figure 2:
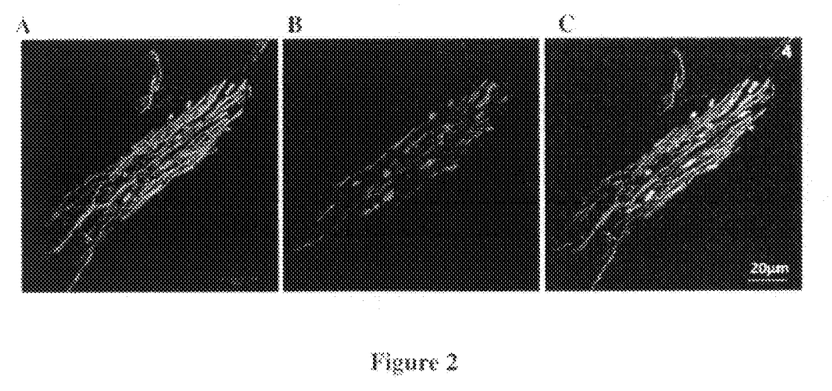
FIG. 2 shows the results of immuno-marking of a healthy deep dermis section with the anti-Nav 1.9 antibody 3881.1 (FIG. 2B) and an anti-peripherin antibody (FIG. 2A). The co-marking is shown in FIG. 2C. A significant proportion of the nerve fibers of the dermis marked with peripherin are also Nav 1.9 positive.

FIGS. 1 and 2 show the marking by immunofluorescence of deep dermis sections with the anti-peripherin antibody (FIG. 2A), the antibody Rbαa6 (FIG. 1B), and the antibody 3881.1 (FIG. 2B). The immuno-marking results obtained with the antibodies Rbαa6 and 3881.1 are similar. An expression of the Nav 1.9 sodium channel localized at the sensitive fibers of the deep dermis is observed. Co-localization areas of peripherin and of Nav 1.9 are shown in FIGS. 1C and 2C.

Figure 3:
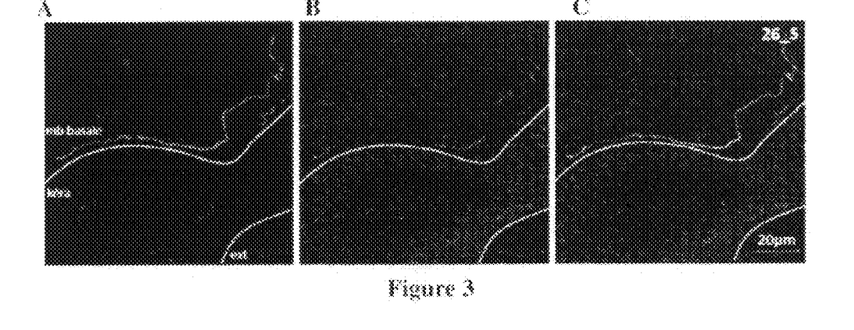
Figure 4:
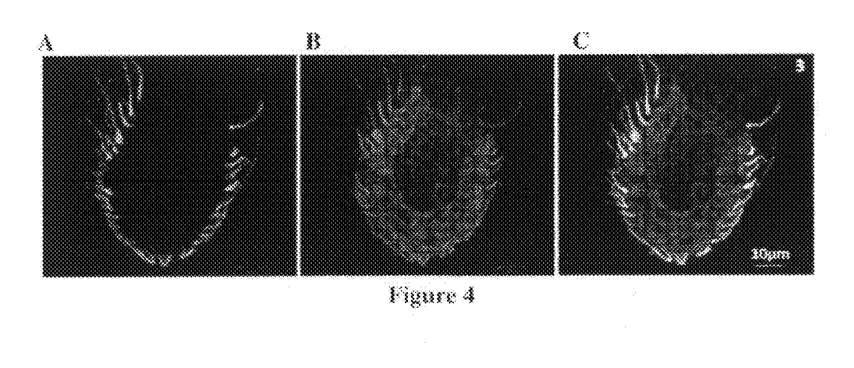

FIGS. 3 and 4 show the immuno-marking results of peripherin and of Nav 1.9 at the epidermis-dermis interface and at a hair follicle respectively. These immuno-marking photographs were obtained with the antibody 3881.1.

FIG. 3 shows the localized expression of Nav 1.9 at an isolated nerve fiber of the dermis. A similar result is observed at the hair follicle where Nav 1.9 is expressed, in a localized way, by the sensitive fibers innervating the follicle. Slight non-specific marking is nevertheless visible of the keratinocytes of the follicle. No significant marking was detected in the epidermis.

Conclusions

These immuno-marking experiments show that the Nav 1.9 sodium channel is expressed in a basal way at the skin sensitive fibers, in particular of the dermis.

Example 2

Over-expression of Nav 1.9 by Skin Sensitive Fibers in Patients Affected with Rosacea Preparation of the Samples The skin samples were prepared in the following way:

After disinfecting the skin, 3 mm skin biopsies were made in a patient affected with rosacea, subject to local anaesthesia at the biopsy site. The biopsy is then washed in PBS pH7.2 and placed in an Eppendorf tube in liquid nitrogen. The Eppendorf is then stored at −80° C. until inclusion into the OCT matrix. The 10 μm thick frozen sections are then made.

Marking Procedure by Immunofluorescence

The immuno-marking procedure is similar to the one described for Example 1

The following antibodies were used:

For peripherin, the primary antibody is a monoclonal antibody (Millipore, MAB1527) of mouse and the secondary antibody is a donkey anti-mouse antibody coupled with Alexa488 (Invitrogen, A-21202).

For Nav 1.9, the primary antibody is the polyclonal rabbit antibody 3881.1 and the secondary antibody is a donkey anti-rabbit antibody coupled with TRITC (Jackson Immunoresearch).

Results

Figure 5:
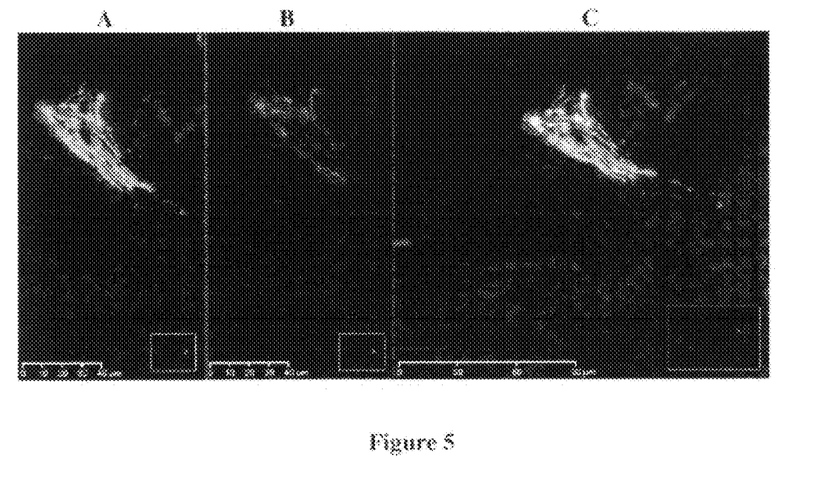
Figure 6:
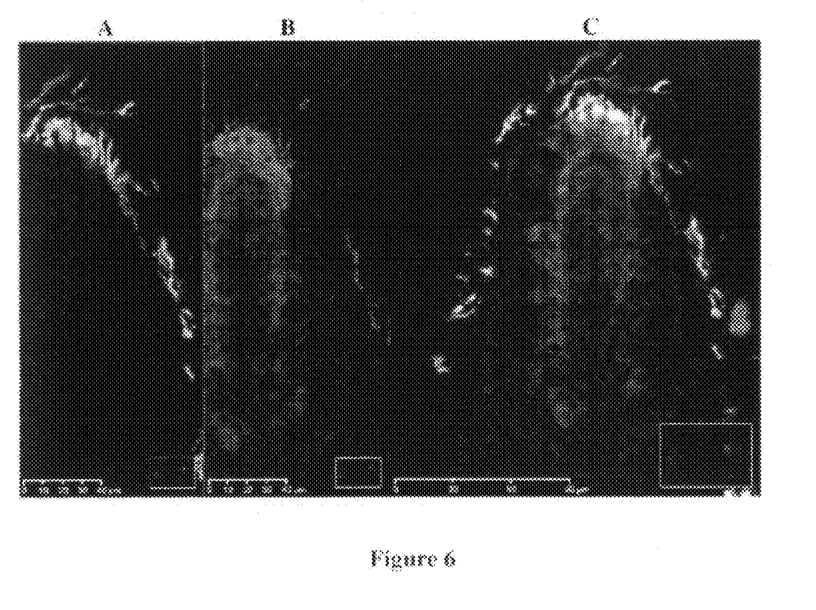
Figure 7:
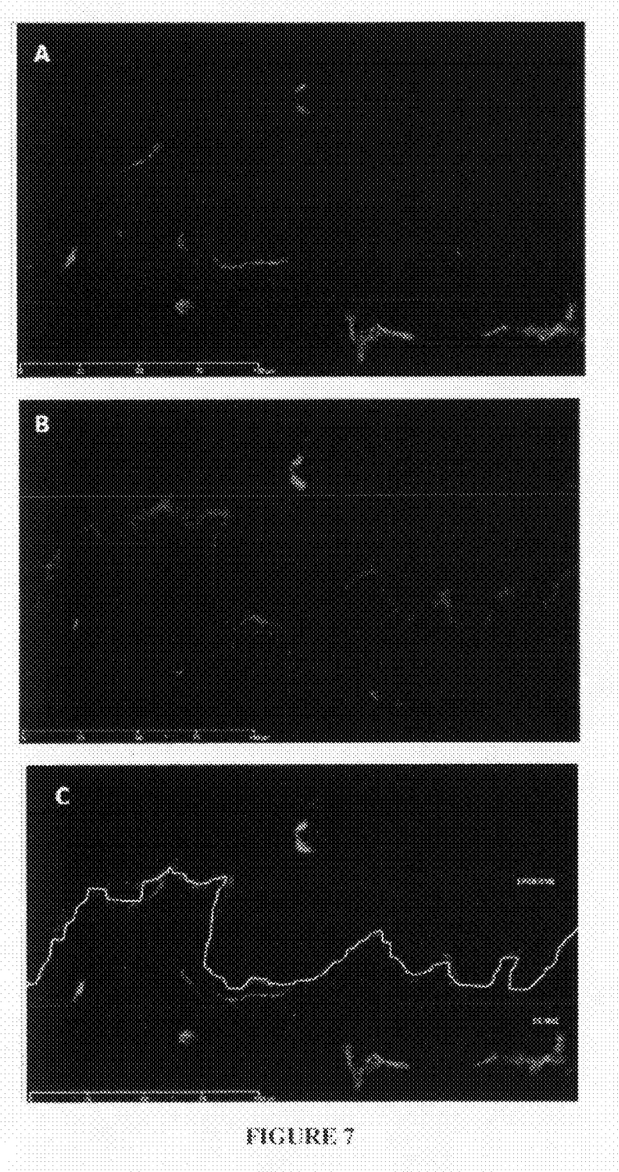

FIGS. 5, 6 and 7 show the immuno-marking results of peripherin and of Nav 1.9 at the dermis, and at a hair follicle from skin samples affected with rosacea. Nav 1.9 is localized at the sensitive fibers of the dermis and of the hair follicle. While a relatively homogenous marking was observed for healthy skin samples, the presence of expression clusters, i.e. localized areas (spots) having very high expression of Nav 1.9 is observed. FIG. 7 moreover shows an expression of Nav 1.9 in the epidermis, which had not been observed for healthy samples.

These preliminary results show an over-expression of Nav 1.9 at skin samples affected with rosacea, in the dermis and the epidermis.

Example 3

Demonstrating the Involvement of the Nav 1.9 Sodium Channel in the Neuro-Inflammatory Response The goal of this study was to demonstrate the impact of Nav 1.9 on the release of the calcitonin gene-related peptide (CGRP). The CGRP peptide is a powerful vasodilator and a mediator of pain at the peripheral and central nervous system. CGRP is also involved in peripheral neurogenic inflammation, in particular of the skin. For this purpose, the Applicant compared the release of CGRP by primary cultures of neurones, after or without treatment with capsaicin. The primary cultures of neurones were obtained from spinal ganglia (dorsal root ganglion—DRG) taken from wild mice (wt) and from mice in which the Nav 1.9 sodium channel gene was invalidated (KO mouse for Nav 1.9).

Primary Cultures of Neurones from Spinal Ganglia of Adult Mice.

The samples of spinal ganglia were made from male C57BL6 mice of 2 to 3 months of age. On average, 20 spinal ganglia were taken per mouse, which corresponds to a total of 50,000 and 80,000 neurones/mouse.

The collected neurones were sown in 96-well plates in amounts of 10,000 cells per well. The wells were covered beforehand with poly-L-Lysine (12 µg/cm²) and laminin (6 µg/cm²) for promoting adhesion of the neurones. The cells were incubated for 24 h at 37° C. before the beginning of the test in a suitable culture medium (D-MEM supplemented with glucose, NEAA, L-glutamine, pyruvate, NGF (Nerve Growth Factor 2.5s mouse submaxillary) GDNF (Glial cell-line Derived Neurotrophic Factor) and fetal calf serum).

All in all, the cell cultures were obtained from 12 mice (6 wild mice and 6 KO mice), 5 to 8 primary culture wells of neurones were prepared per mouse.

Quantification of the Release of CRGP in the Medium after Treatment with Capsaicin A portion of the primary cultures (3 to 5 culture wells per mouse) were incubated for 15 min in the presence of capsaicin at 300 nM. The second portion of the primary cultures (2 to 3 culture wells per mouse) did not undergo any treatment.

The dosage of the CRGP released in the supernatant was achieved by ELISA assay by using the kit SPlbio ref. A05482 intended for dosing rat CRGP, but which may also be used for quantifying mouse CRGP.

Briefly, the supernatants of the primary cultures were taken and diluted to ⅕ before being added into the wells of a microplate covered with an anti-CGRP monoclonal antibody. A second anti-CRPG antibody (polyclonal), coupled with acetylcholine esterase, was then added. After incubation and rinsing, the detection was achieved by means of Ellman's reagent (DTNB) by measuring absorbance at 405 or 414 nm.

Results

Figure 8A:
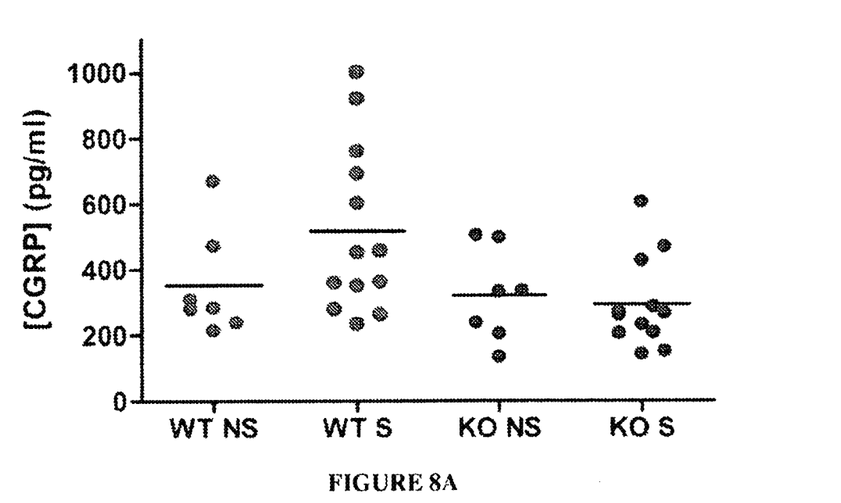
Figure 8B:
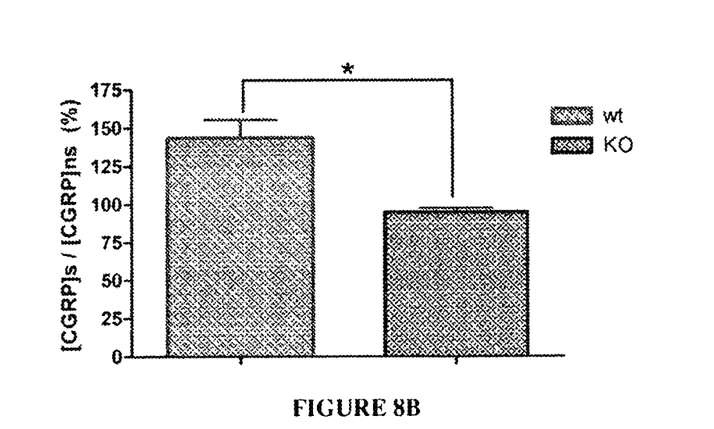

The results are illustrated by FIGS. 8A and 8B.

For the primary cultures obtained from wild mice (WT), it is observed that the treatment with capsaicin caused a significant increase in the amount of CGRP (+43.5%) present in the supernatant. On the other hand, no variation in the amount of CGRP released in the supernatant was observed for the primary cultures from KO mice. With or without treatment with capsaicin, the amount of CGRP detected in the supernatant is equivalent to the basal level of CGRP of the supernatant of the WT cells (before stimulation with capsaicin).

Nav 1.9 is therefore involved in the regulation of the release of CGRP consecutively to stimulation with capsaicin.

Example 4

Quantification of the Intracellular Pool of CGRPs in Neurone Cultures Obtained from Wild Mice (WT) and KO Mice for Nav 1.9 (KO)

Primary Cultures of Neurones from Spinal Ganglia of Adult Mice.

The procedure used is identical with that of Example 3. The primary neurone cultures were prepared from 4 KO mice and 4 WT mice.

Dosage of the Intracellular Pool of CGRP.

After incubation for 24 h at 37° C. and rinsing, the primary cultures were lyzed with Triton X100 at 1%. The dosage of the CGRP peptide in the cell lyzates was carried out with the ELISA test described in Example 3.

It is found that the average CRPG concentration in the primary cultures from KO mice is slightly less than the one obtained for primary cultures from wild mice. Nevertheless, the observed difference is not significant.

Accordingly, the releasing difference of CGRP, under stimulation with capsaicin, observed for primary neurone cultures WT and KO, in Example 3, cannot be ascribed to an intracellular deficiency in CGRP in KO primary neurone cells.

CONCLUSION

The results of release of the CGRP peptide by primary neurone cultures from WT and KO mice, after or without stimulation with capsaicin, and the immuno-marking results of dermis sections very strongly suggest that the involvement of Nav 1.9 in the potentialization of the neurogenic inflammation observed at the skin in the inflammatory skin pathologies. Nav 1.9 is therefore a therapeutic target of interest for treating inflammatory skin diseases, in particular rosacea.

The invention claimed is:

1. An in vitro method for identifying a compound intended for the treatment of an inflammatory skin disease, the method comprising:
   a) measuring, in the absence of the compound, expression or activity of Nav 1.9 sodium channel in a cell capable of expressing Nav 1.9 sodium channel,
   b) incubating the cell with the compound,
   c) measuring expression or activity of Nav 1.9 sodium channel in the cell after incubation with the compound,
   d) identifying the compound as a modulator of Nav 1.9 sodium channel expression or activity based on a difference of expression or activity of Nav 1.9 sodium channel in steps a) and b), and
   e) testing the selected compound on an inflammatory skin disease model, wherein the inflammatory skin disease is selected from the group consisting of rosacea, psoriasis, pruritus, eczema and atopic dermatitis.

2. The in vitro screening method according to claim 1, wherein the skin disease is selected from the group consisting of erythematotelangiectatic rosacea (subtype I), papulopustular rosacea (subtype II), phymatous rosacea (subtype III), ocular rosacea (subtype IV) and a granulomatous variant of rosacea.

3. The in vitro screening method according to claim 1, wherein the skin disease is selected from the group consisting of atopic eczema, contact eczema and nummulur eczema.

4. The in vitro screening method according to claim 1, wherein the skin disease is atopic eczema.

5. The in vitro screening method according to claim 1, wherein the compound is selected from the group consisting of an inorganic molecule, a toxin, a protein, a peptide, an organic synthetic molecule, an antibody directed against Nav 1.9 sodium channel, and a molecule comprising a fragment of an antibody directed against Nav 1.9 sodium channel.

6. The in vitro screening method according to claim 5, wherein the organic synthetic molecule has a molecular weight of at most 1,000 g/mol.

7. The in vitro screening method according to claim 5, wherein the antibody directed against Nav 1.9 sodium channel is a chimeric or humanized, human, monoclonal antibody.

8. The in vitro screening method according to claim 5, wherein the fragment of an antibody directed against Nav 1.9 sodium channel is selected from the group consisting of ScFv, VH, VHH, VNAR, a Fab', a F(ab')2, a bispecific antibody, and the humanized or chimeric versions thereof.

9. The in vitro screening method according to claim 1, wherein the compound is an inhibitor of the translation or of the transcription of the Nav 1.9 sodium channel gene, or a compound capable of inducing catabolism of Nav 1.9 sodium channel.

10. The in vitro screen method according to claim 1, wherein incubating the cell with the compound causes a variation of at least 10% of the expression level of Nav 1.9 sodium channel in the cell as compared with a cell which has not been incubated with the compound.

11. The in vitro screening method according to claim 10, wherein the variation of the expression level of Nav 1.9 sodium channel in the cell is at least 20% as compared with a cell which has not been incubated with the compound.

12. The in vitro screening method according to claim 1, wherein a binding affinity of the compound for Nav 1.9 sodium channel is more than the binding affinity of the compound for other sodium channels.

13. The in vitro screening method according to claim 1, wherein the dissociation constant (Kd) of the compound for Nav 1.9 sodium channel is at least 10 times less than the dissociation constant of the compound for the other sodium channels.

14. The in vitro screening method according to claim 13, wherein the dissociation constant (Kd) of the compound for Nav 1.9 sodium channel is at least 100 times less than the dissociation constant of the compound for the other sodium channels.

15. The in vitro screening method according to claim 14, wherein the dissociation constant (Kd) of the compound for Nav 1.9 sodium channel is at least 1,000 times less than the dissociation constant of the compound for the other sodium channels.

16. The in vitro screening method according to claim 1, wherein the compound inhibits the expression or the activity of Nav 1.9 sodium channel if the expression or activity level of Nav 1.9 sodium channel in the cell incubated with the compound is at most equal to 90% of the expression or activity level of Nav 1.9 sodium channel detected in a control cell which has not been incubated with the compound.

17. The in vitro screening method according to claim 16, wherein the expression or activity level of Nav 1.9 sodium channel in the cell incubated with the compound is at most equal to 80% of the expression or activity level of Nav 1.9 sodium channel detected in a control cell which has not been incubated with the compound.

18. An in vitro method for identifying a compound intended for the treatment of an inflammatory skin disease, the method comprising:
 a) measuring, in the absence of the compound, expression or activity of Nav 1.9 sodium channel in a cell capable of expressing Nav 1.9 sodium channel,
 b) incubating the cell with the compound,
 c) measuring expression or activity of Nav 1.9 sodium channel in the cell after incubation with the compound,
 d) identifying the compound as a modulator of Nav 1.9 sodium channel expression or activity based on a difference of expression or activity of Nav 1.9 sodium channel in steps a) and c), and
 e) testing the selected compound on an inflammatory skin disease model,
 wherein the compound is selected from the group consisting of an inorganic molecule, a toxin, a protein, a peptide, an organic synthetic molecule, an antibody directed against Nav 1.9 sodium channel, and a molecule comprising a fragment of an antibody directed against Nav 1.9 sodium channel.

19. An in vitro method for identifying a compound intended for the treatment of an inflammatory skin disease, the method comprising:
 a) measuring, in the absence of the compound, expression or activity of Nav 1.9 sodium channel in a cell capable of expressing Nav 1.9 sodium channel,
 b) incubating the cell with the compound,
 c) measuring expression or activity of Nav 1.9 sodium channel in the cell after incubation with the compound,
 d) identifying the compound as a modulator of Nav 1.9 sodium channel expression or activity based on a difference of expression or activity of Nav 1.9 sodium channel in steps a) and c), and
 e) testing the selected compound on an inflammatory skin disease model,
 wherein incubating the cell with the compound causes a variation of at least 10% of the expression level of Nav 1.9 sodium channel in the cell as compared with a cell which has not been incubated with the compound.

20. The in vitro screening method according to claim 19, wherein the variation of the expression level of Nav 1.9 sodium channel in the cell is at least 20% as compared with a cell which has not been incubated with the compound.

* * * * *